United States Patent
Arnold et al.

(10) Patent No.: US 7,491,491 B2
(45) Date of Patent: Feb. 17, 2009

(54) DETECTING AND/OR MEASURING A SUBSTANCE BASED ON A RESONANCE SHIFT OF PHOTONS ORBITING WITHIN A MICROSPHERE

(75) Inventors: Steven Arnold, New York, NY (US); Iwao Teraoka, Rye, NY (US)

(73) Assignee: Polytechnic Institute of New York University, Brooklyn, NY (US)

( * ) Notice: Subject to any disclaimer, the term of this patent is extended or adjusted under 35 U.S.C. 154(b) by 1092 days.

(21) Appl. No.: 10/096,333

(22) Filed: Mar. 12, 2002

(65) Prior Publication Data

US 2003/0174923 A1    Sep. 18, 2003

(51) Int. Cl.
*C12Q 1/68* (2006.01)

(52) U.S. Cl. .......................................................... 435/6

(58) Field of Classification Search .................. 435/6, 435/4, 7.1, 7.91, 7.92, 7.93, 7.94, 7.95, 283.1, 435/287.3, 287.9, 288.7; 436/514, 517, 518, 436/523–528; 422/50, 55, 56–60
See application file for complete search history.

(56) References Cited

U.S. PATENT DOCUMENTS

| | | | |
|---|---|---|---|
| 4,169,804 A | 10/1979 | Yapel, Jr. | |
| 5,231,533 A | 7/1993 | Gonokami et al. | |
| 5,459,194 A * | 10/1995 | Larson | 524/506 |
| 5,496,997 A | 3/1996 | Pope | |
| 5,598,005 A * | 1/1997 | Wang et al. | 250/459.1 |
| 5,786,219 A | 7/1998 | Zhang et al. | |
| 6,266,459 B1 | 7/2001 | Walt et al. | |
| 6,389,197 B1 | 5/2002 | Iltchenko et al. | |
| 6,490,039 B2 | 12/2002 | Maleki et al. | |
| 6,583,399 B1 | 6/2003 | Hunziker et al. | |
| 6,649,719 B2 * | 11/2003 | Moore et al. | 526/245 |
| 6,720,007 B2 * | 4/2004 | Walt et al. | 424/489 |
| 6,781,696 B1 * | 8/2004 | Rosenberger et al. | 356/437 |
| 6,824,975 B2 * | 11/2004 | Hubscher et al. | 435/4 |
| 6,859,570 B2 * | 2/2005 | Walt et al. | 385/12 |
| 7,012,687 B2 * | 3/2006 | Blumberg et al. | 356/301 |
| 2001/0033587 A1 | 10/2001 | Painter et al. | |
| 2002/0037132 A1 | 3/2002 | Sercel et al. | |
| 2002/0041730 A1 | 4/2002 | Sercel et al. | |
| 2002/0044739 A1 | 4/2002 | Vahala et al. | |
| 2002/0080842 A1 | 6/2002 | An et al. | |
| 2002/0081055 A1 | 6/2002 | Painter et al. | |
| 2002/0122615 A1 | 9/2002 | Painter et al. | |

OTHER PUBLICATIONS

Vollmer, Frank; Arnold, Stephen; Braun, Dieter; Teraoka, Iwao; "Multiplexed DNA Quantification by Spectroscopic Shift of Two Microsphere Cavities," Biophysical Journal, vol. 85, Sep. 2003 (1974-1979).

Cai, Ming; Hunziker, Guido; Vahala, Kerry; "Fiber-Optic Ad-Drop Device Based on a Silica Microsphere-Whispering Gallery Mode System," IEEE Photonics Technology Letters, vol. 11, No. 6, (Jun. 1999).

A. Serpengüzel, S. Arnold and G. Griffel, "Excitation of resonances of microspheres on an optical fiber," *Optics Letters*, vol. 20, No. 7, pp. 654-656, (Apr. 1995).

S. Arnold, "Microspheres, Photonic Atoms and the Physics of Nothing," *American Scientist*, vol. 89, pp. 414-421 (Sep.-Oct. 2001).

* cited by examiner

*Primary Examiner*—Ann Lam
(74) *Attorney, Agent, or Firm*—Straub and Pokotylo; John C. Pokotylo

(57) ABSTRACT

Detecting and/or measuring a substance based on a resonance shift of photons orbiting within a microsphere of a sensor. Since the resonance of the microsphere has a large quality factor, the sensor is extremely sensitive. The sensor includes the microsphere coupled with at least one optical fiber. The surface of the microsphere includes receptors complementary to the substance. The at least one optical fiber can be provided with at least one additional microsphere having a surface free of the receptors. Resonance shifts observed in such an additional microsphere(s) can be attributed to factors unrelated to the presence of the substance. The resonance shift observed in the microsphere with the receptors can be compensated based on the resonance shift of the additional microsphere(s) to remove the influence of these other factors.

28 Claims, 15 Drawing Sheets

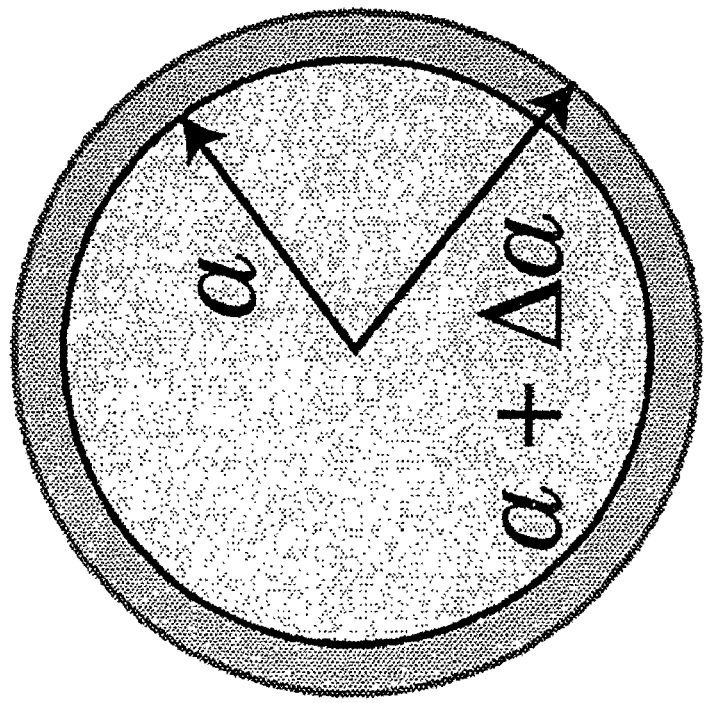
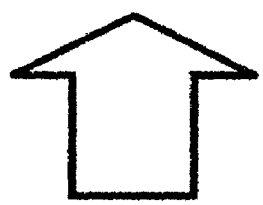
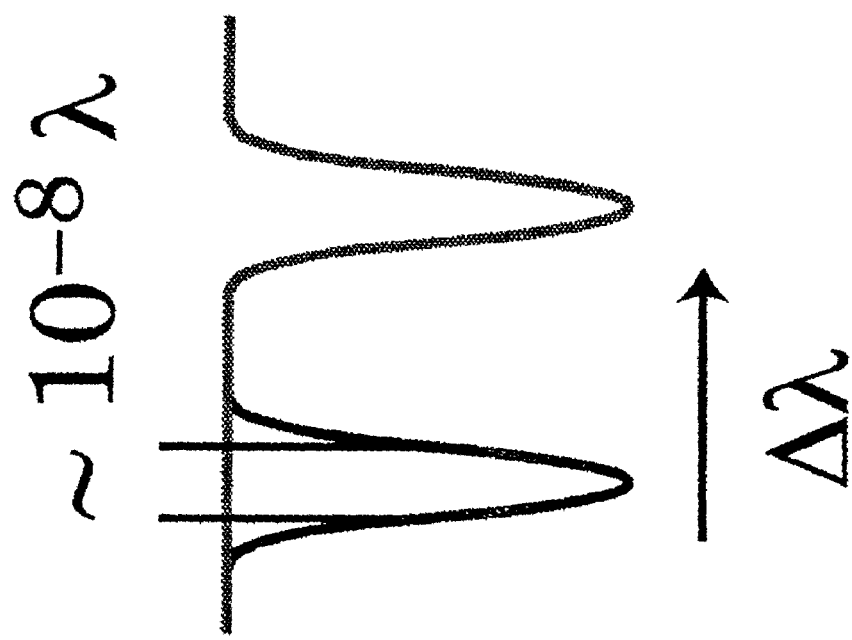
FIGURE 4

1800

1900

DETECTING AND/OR MEASURING A SUBSTANCE BASED ON A RESONANCE SHIFT OF PHOTONS ORBITING WITHIN A MICROSPHERE

§ 1. BACKGROUND

§ 1.1 Field of the Invention

The present invention concerns detecting the presence of, and/or measuring the amount or concentration of substances, such as chemical and/or biological substances for example. More specifically, the present invention concerns detecting and/or measuring a substance based on a resonance shift of photons orbiting within a microsphere.

§ 1.2 Related Art—Measurement Principle Using Ray Optics In Microscopic Having a Changing Size Resonances in a geometrical optics limit are associated with the optical ray paths, such as those 110 illustrated in the cross section of a particle 100 illustrated in FIG. 1. Total internal reflection keeps the photon(s) from radiating outward. Collectively, the ray path segments 110 define a polygon.

Basically, the light circles (or orbits) the interior of the particle 100, returning in phase. This is known as a mode of the first order. For higher order modes, the photon(s) takes several orbits before its ray path closes—i.e., before the photon returns in phase.

The foregoing illustration and assumptions are appropriate for meso-optic elements (i.e., devices, comparable in size to the wavelength of light, that can confine photons) 100 having a diameter $2a$ that is between 10 and 100 times the wavelength of the photon. The resonances have specific polarization states.

Referring to FIG. 2, an optical fiber 200 may be evanescently coupled with a microsphere 100'. More specifically, an evanescent electromagnetic field associated with total internal reflection exists just outside the microsphere 100', decaying exponentially as a function of distance, typically over a distance of ~0.1 µm. Further, internal reflection on a curved surface induces a small amount of radiation leakage in the far field. The higher the order of the mode, the greater the leakage. For example, the energy loss in one oscillation within slightly spheroidal fused silica microspheres ($2a$>~50 µm) has been measured to be smaller than 2 billionths of the energy contained, yielding a quality factor $Q$>~$10^8$. Stated in another way, the linewidth of the associated resonance ($\delta f$) in the spectrum is 10 billionth of the frequency ($\delta f=f/Q$). Referring to FIG. 3, the resonance modes can be detected as transmission dips 300 in the evanescently coupled optical fiber 200.

As illustrated in FIG. 4, if the size (or shape, or refractive index) of the particle 100/100' changes, the resonances shift in frequency. For example, in the case of a sphere, as its radius increases, the resonance occurs at a longer wavelength. This shift can be expressed as:

$$\frac{\Delta a}{a} = \frac{\Delta \lambda}{\lambda} \quad (1)$$

This relationship may be derived as follows.

When considering size sensitivity, recognize that the angular momentum L of the photon in a given mode is quantized.

That is $$L = \left(\frac{h}{2\pi}\right)\sqrt{l(l+1)},$$

where l is an integer and h is Plank's constant. The angular momentum in the geometry of FIG. 1 is equal to its linear momentum (p) times the distance of the closest approach from the sphere center (a $\cos(\pi/q)$), where q is the number of reflections in the orbit. The linear momentum p of the photon is its energy (hf) divided by the speed of light in the medium. That is, p=hfn/c, where f is the frequency, n is the refractive index of the sphere, and c is the speed of light in vacuum. Consequently, the angular momentum may be expressed as:

$$L = \frac{hfna}{c}\cos\frac{\pi}{q} = \frac{hna}{\lambda}\cos\frac{\pi}{q} \quad (2)$$

where $\lambda$ is the wavelength in vacuum.

Since the resonance mode has a constant angular momentum, equation (2) can be used to estimate the effect that various perturbations have on the resonance wavelength. For example, to reiterate, as was illustrated in FIG. 4, if the size (or shape, or refractive index) of the particle 100/100' changes, the resonances shift in frequency. In the case of a sphere, as its radius increases, the resonance occurs at a longer wavelength. This shift can be expressed as:

$$\frac{\Delta a}{a} = \frac{\Delta \lambda}{\lambda} \quad (1)$$

The sensitivity of this measurement technique can be estimated as follows. If it is assumed that the linewidth ($\delta\lambda \cong 10^{-8}\lambda$), then the smallest "measurable" size change is $|\Delta a|_{min}=10^{-8}a$. Assuming a sphere radius (a) on the order of 10 µm, $|\Delta a|_{min}=10^{-13}$ m. This is much smaller than the size of an atom.

Unfortunately, the resonance of photon(s) orbiting within a microsphere is fairly sensitive to changes in temperature. To estimate the resonance shift due to temperature change, both the radius and refractive index (n) of the microsphere are permitted to vary. Based on equation (2), the fractional shift in wavelength may be expressed as:

$$\frac{\Delta \lambda}{\lambda} = \frac{\Delta a}{a} + \frac{\Delta n}{n} \quad (3)$$

In most amorphous optical materials, both the size and the refractive index will change approximately linearly with temperature at near room temperature. Thus, there is a need for improving the foregoing technique of detecting and/or measuring a substance based on a resonance shift of photons orbiting within a microsphere, by making it insensitive or less sensitive to changes in temperature. Indeed, it would be useful to make the foregoing technique insensitive or less sensitive to changes other than changes in the amount or concentration of the substance being detected or measured.

Other challenges to using the foregoing technique include (i) connecting the microsphere to the optical fiber to ensure adequate mechanical reliability and adequate optical coupling, and (ii) attaching receptors to the microsphere.

§ 2. SUMMARY OF THE INVENTION

The present invention may provide a detection and/or measurement technique based on a resonance shift in photons orbiting within a microsphere. The present invention may do so by applying a light source to a sensor including a microsphere coupled with an optical carrier, detecting light at the other end of the optical carrier, and determining adsorption of a material onto the microsphere based on the detected light.

The present invention may also provide improved techniques for attaching a microsphere to optical fiber. The present invention may do so by eroding cladding from the optical fiber and using a siloxane network to bridge a silica fiber and a silica microsphere, or using amide and/or other bonds to bridge a silica microsphere and a silica fiber, or attaching carboxulic acid to the eroded fiber with a copolymer of methyl methacylate and acrylic acid in solution, and bridging the two carboxylic groups.

The present invention may also provide improved techniques for attaching receptors to a microsphere. The present invention may do so by covalently bonding complementary oligonucleotides to the surface of a microsphere, covalently attaching an antibody to the surface of a microsphere, or immobilizing an enzyme on the microsphere.

Finally, the present invention may provide an improved detection and/or measurement technique, based on a resonance shift in photons orbiting within a microsphere, that is insensitive or less sensitive to changes in temperature or other factors unrelated to the presence or concentration of the substance being detected or measured. The present invention may do so by providing a sensor with multiple microspheres and distinguishing resonance shifts due to common mode noise from resonance shifts due to the adsorption of a substance onto at least one of the microspheres.

§ 3. BRIEF DESCRIPTION OF THE DRAWINGS

FIG. 4 illustrates the shift in resonance of photon(s) orbiting within a sphere as the size of the sphere changes.

§ 4. DETAILED DESCRIPTION OF THE INVENTION

The present invention involves novel methods and apparatus for detecting and/or measuring a substance based on a shift in resonance of photon(s) orbiting within a microsphere. The following description is presented to enable one skilled in the art to make and use the invention, and is provided in the context of particular embodiments and methods. Various modifications to the disclosed embodiments and methods will be apparent to those skilled in the art, and the general principles set forth below may be applied to other embodiments, methods and applications. Thus, the present invention is not intended to be limited to the embodiments and methods shown and the inventors regard their invention as the following disclosed methods, apparatus and materials and any other patentable subject matter to the extent that they are patentable.

§ 4.1 Exemplary Applications

The present invention may be used in detecting and/or measuring substances, such as chemical or biological substances for example. The particular substance to be detected and/or measured may affect the design (e.g., size, material, etc.) of the microsphere, as well as the choice of receptors. Exemplary sensors, used to detect RNA, DNA strands, antigens, bacteria, and other biological substances, as well as chemical substances, are described in § 4.4.2 below.

§ 4.2 Functions that May be Performed

The present invention may function to detect and/or measure a substance based on a resonance shift of photons orbiting within a microsphere. The present invention may also function to attach a microsphere to optical fiber. The present invention may also function to attach receptors to a microsphere. Finally, the present invention may function to improve detection and/or measurement, based on a resonance shift of photons orbiting within a microsphere, by eliminating or reducing sensitivity to changes in temperature or other factors unrelated to the presence or concentration of the substance being detected or measured.

§ 4.3 Exemplary Operations

Figure 5:
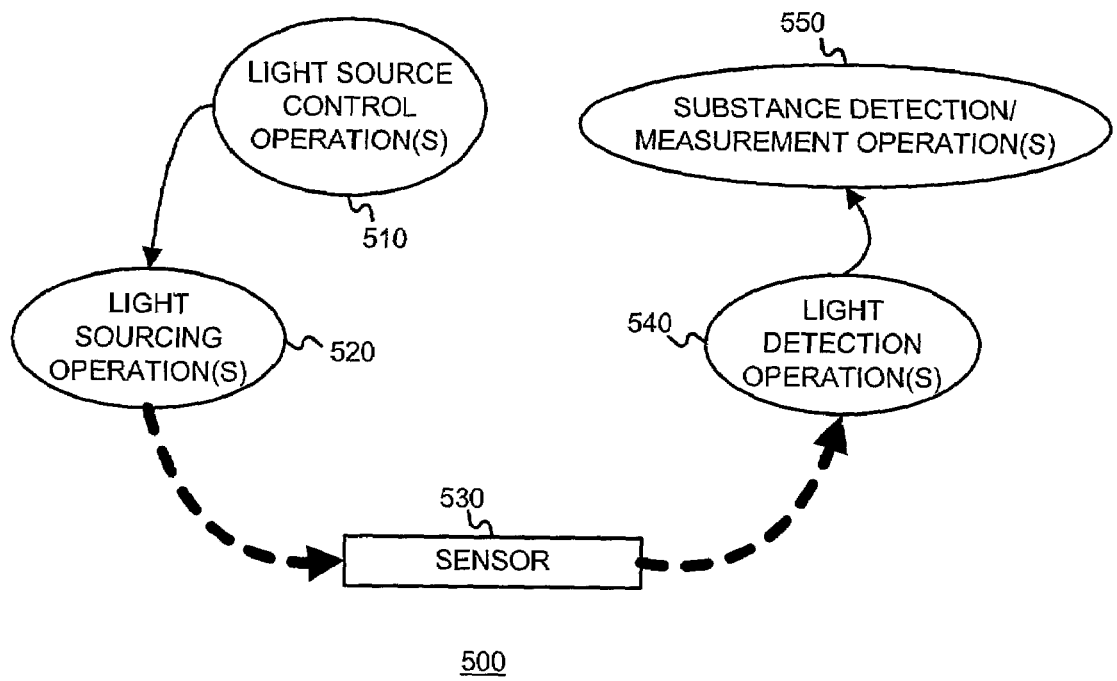
FIG. 5 illustrates operations that may be performed by a system for detecting and/or measuring a substance based on a resonance shift of photons orbiting within a microsphere.

FIG. 5 is a bubble chart illustrating operations that may be performed in detecting and/or measuring a substance in accordance with the present invention. A light sourcing operation 520 may emit a light, under the control of a light source control operation 510, into (or through) a sensor 530. A detection operation 540 may detect light from the sensor 530. Certain detected properties of the light may then be provided to detection and/or measurement operation(s) 550. Exemplary methods and apparatus that may be used to effect these various operations are described in § 4.4.1 below.

Figure 6:
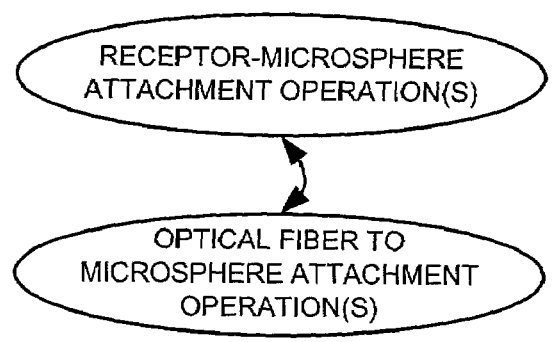
FIG. 6 illustrates operations that may be performed when fabricating a sensor head for use in a system, such as that illustrated in FIG. 5, for detecting and/or measuring a substance based on a resonance shift of photons orbiting within a microsphere.

Certain aspects of the present invention concern the fabrication of a sensor to be used in a system such as that illustrated in FIG. 5. FIG. 6 is a bubble chart illustrating operations that may be performing in fabricating a sensor in accordance with the present invention. Basically, the fabrication of a sensor in accordance with the present invention may include two operations—attaching 610 the receptor(s) to the microsphere(s), and coupling 620 the microsphere(s) to the optical fiber. Exemplary methods, apparatus and materials that may be used to effect these various operations are described in § 4.4.2 below.

§ 4.4 Exemplary Methods and Apparatus for Performing the Exemplary Operations Exemplary methods and apparatus that may be used to perform operations related to detecting and/or measuring a substance are described in § 4.4.1 below. Then, exemplary methods, apparatus and compositions of matter that may be used to perform operations related to fabricating sensors are described in § 4.4.2 below.

§ 4.4.1 Exemplary Methods and Apparatus for Performing Operations Related to Detecting and/or Measuring Substances In the following, exemplary apparatus for detecting and/or measuring substances are described in § 4.4.1.1, while exemplary methods are described in § 4.4.1.2.

§ 4.4.1.1 Exemplary Apparatus for Detecting and/or Measuring Substances

Figure 7:
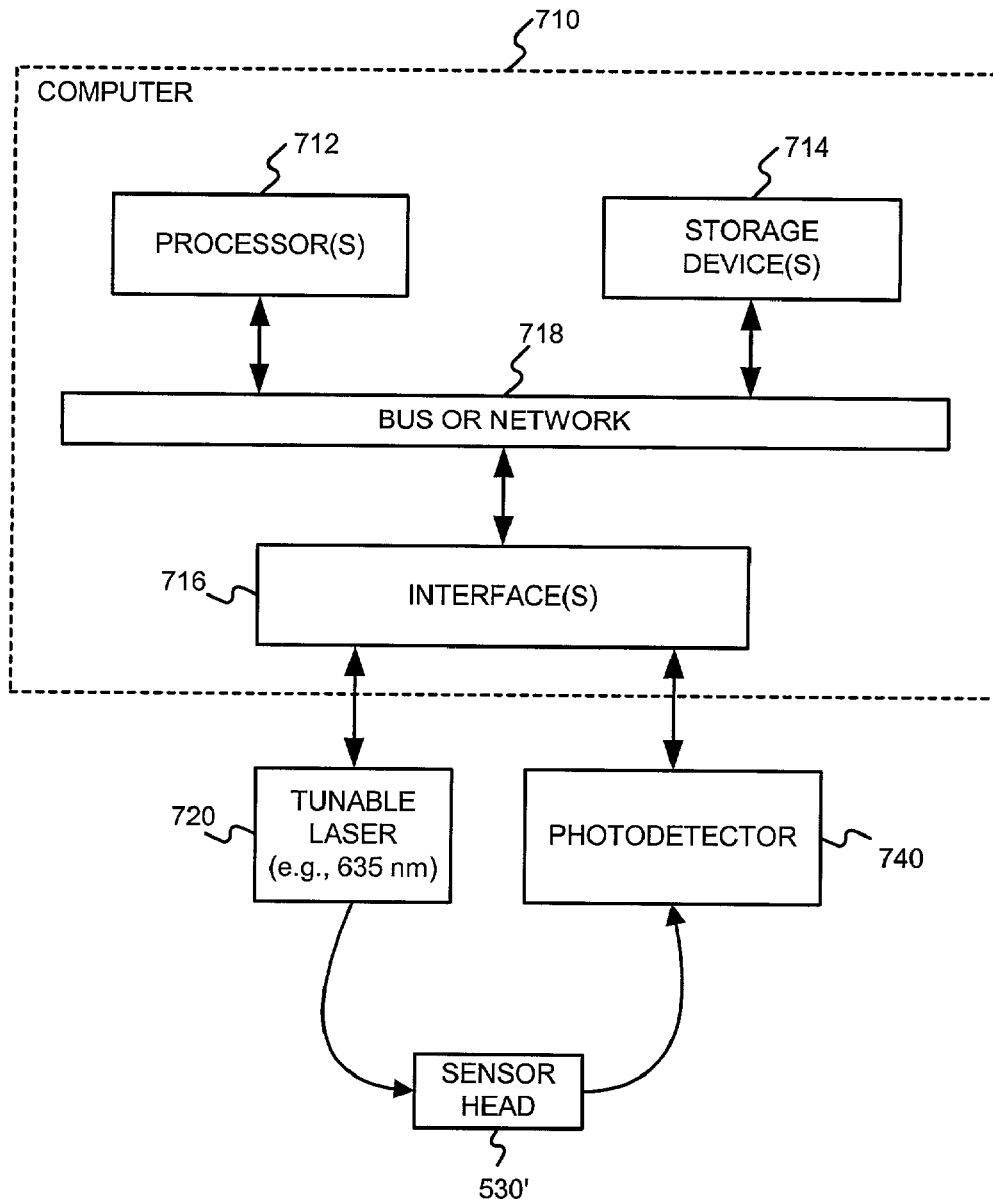
FIG. 7 illustrates an exemplary system for detecting and/or measuring a substance based on a resonance shift of photons orbiting within a microsphere.

FIG. 7 is a block diagram of a system 700 that may be used to effect the operations of FIG. 5. A computing device, such as a personal computer for example, may function to (a) control a tunable laser 720, and (b) to determine the existence or amount of a substance based on the output of a photodetector 740.

§ 4.4.1.1.1 Exemplary Light Source

As can be appreciated from the foregoing, the tunable laser 720 may effect the light sourcing operation(s) 520. An exemplary tunable laser 720 is the model 2010A, available from Newport Corporation of Irvine, Calif., which permits scanning the CW laser with an external cavity. The tuning range of the exemplary laser 720 may be ±4 nm with the center wavelength at 635 nm. The linewidth of the exemplary laser 720 may be less than 1 kHz, with a resolution on the order of $10^{-11}$.

§ 4.4.1.1.2 Exemplary Detector

As can also be appreciated from the foregoing, the detector 740 may effect the light detecting operation(s) 540. An exemplary detector 740 is the model PDA55 broadband photodiode detector available from Thorlabs, Inc. of Newton, N.J. The output of the detector may be digitized by an analog-to-digital converter, such as the 16-bit, 200 kHz model PCI-6034E from National Instruments Corporation of Austin, Tex., in the personal computer.

§ 4.4.1.1.3 Exemplary Sensing Heads

Although not shown, standard optical fiber connectors may be provided to facilitate the exchange of sensing heads 530.

The sensing head 530 may have a number of possible configurations, two of which are described in detail below. The first sensing head configuration is referred to as a single-sphere sensing head. The second sensing head configuration is referred to as a multiple-sphere sensing head. In either case, the radius of the microsphere(s) preferably ranges from about 2 μm to about 1 mm, and more preferably is from about 10 μm to about 100 μm.

§ 4.4.1.1.3.1 Single-Sphere Sensing Head

Figure 8:
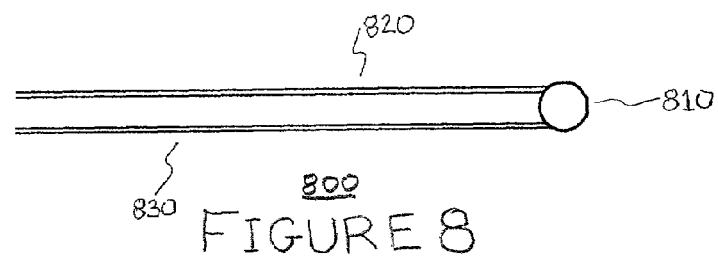
FIG. 8 illustrates a single-sphere sensor head that may be used in a system for detecting and/or measuring a substance based on a resonance shift of photons orbiting within a microsphere.
Figure 9:
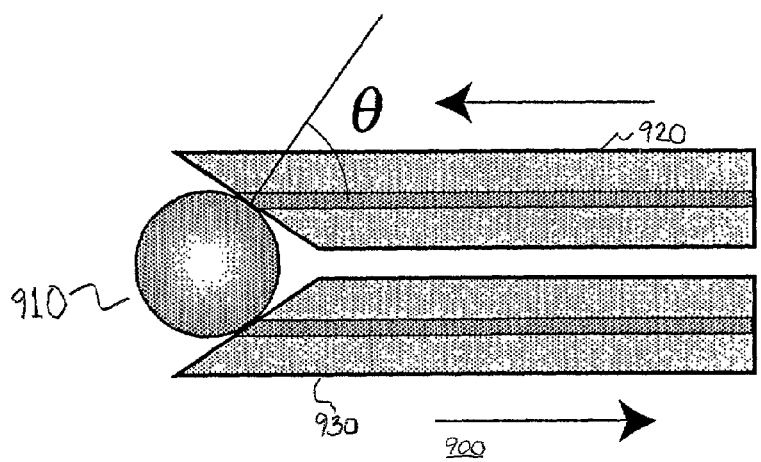
FIG. 9 illustrates an exemplary single-sphere sensor.

As shown in FIG. 8, an exemplary single-sphere sensing head 800 may include a microsphere 810 positioned at the end of a pair of optical fibers 820/830. One of the optical fibers 820 is optically coupled with a light source, while the other is optically coupled with a photodetector. For example, FIG. 9 is a cross-section of a possible design for a single-sphere sensing head 900 including a microsphere 900 positioned at the end of a pair of optical fibers 920/930. Light directed through optical fiber 920 toward the microsphere 910 may reach the beveled surface of the fiber at an angle θ, such as the one greater than the critical angle $\theta_c$ (sin $\theta_c = n_{sphere}/n_{core}$, where $n_{sphere}$ and $n_{core}$ are the refractive indices of the sphere and the fiber core, respectively). The evanescent field just outside the optical fiber 920 couples to the evanescent field of a particular resonant mode of the microsphere 910. The other optical fiber 930 senses this evanescent field around the microsphere 910. Consequently, peaks can be observed in the outgoing optical fiber 930 at the resonant frequencies. An exemplary single-sphere sensing head having the general features as that 900 illustrated in FIG. 9 may be fabricated in the manner described in § 4.4.2 below.

§ 4.4.1.1.3.2 Multiple-Sphere Sensing Head

A multiple-sphere sensing head will now be described. First, however, the challenges that led to the multiple-sphere sensing head are introduced. Recall that the resonance characteristics of a microsphere are based on (i) the size of the microsphere, (ii) the shape of the microsphere, (iii) the refractive indices of the microsphere and the surrounding medium, and (iv) the adsorption of the microsphere. Some of these factors will be influenced by the local temperature, the stress on the microsphere, and the concentration or the presence of the substance to be measured in the surrounding medium (e.g., fluid). Recall also that the sensitivity of the resonance frequencies to changes in temperature is relatively high. Indeed, the resonance frequencies of the microsphere may be extremely susceptible to environmental disturbances. For example, a slight drift in temperature, or pressure of the surrounding medium, or a change in a solvent composition (and consequently, its refractive index) in which the microsphere is placed, may cause a large change in the resonance characteristics, perhaps exceeding the change caused by the adsorption of the substance or the presence of the substance in close proximity of the microsphere surface. A multiple-sphere sensing head will mitigate or eliminate these problems.

Figure 10:
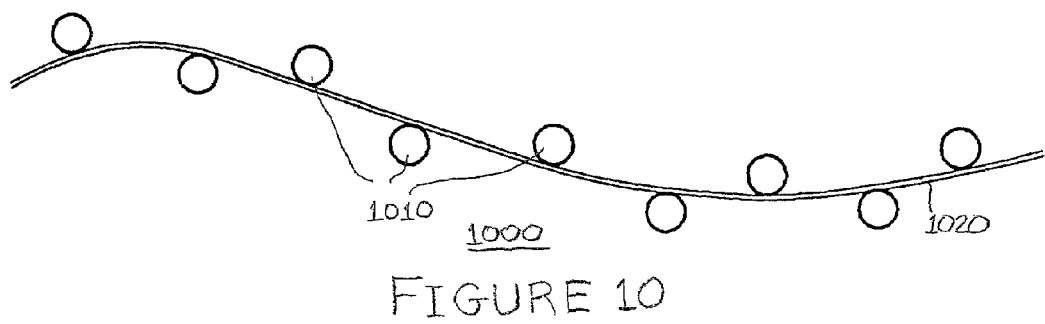
FIG. 10 illustrates a multiple-sphere sensor head that may be used in a system for detecting and/or measuring a substance based on a resonance shift of photons orbiting within a microsphere.

As shown in FIG. 10, an exemplary multiple-sphere sensing head 1000 may include at least two microspheres 1010 coupled with an optical fiber 1020. One end of the optical fiber 1020 is optically coupled with a light source, while the other end is optically coupled with a photodetector. In one embodiment, the surface of each microsphere 1010 is modified with a receptor to interact with a specific ligand, though at least one of the microspheres may 1010 remain unmodified. In such an embodiment, changes due to the environmental disturbances affect the resonance characteristics for all of the microspheres 1010 in the same way. This affect on the resonance characteristics of the microspheres 1010 can be characterized as "common-mode noise". On the other hand, the adsorption of a specific ligand will affect only the microsphere(s) 1010 having the associated receptor. The common-mode noise can be removed from the signal using wavelength screening and spectrum interpretation. An example of this is illustrated in FIGS. 11, 12A, 12B and 13.

Figure 11:
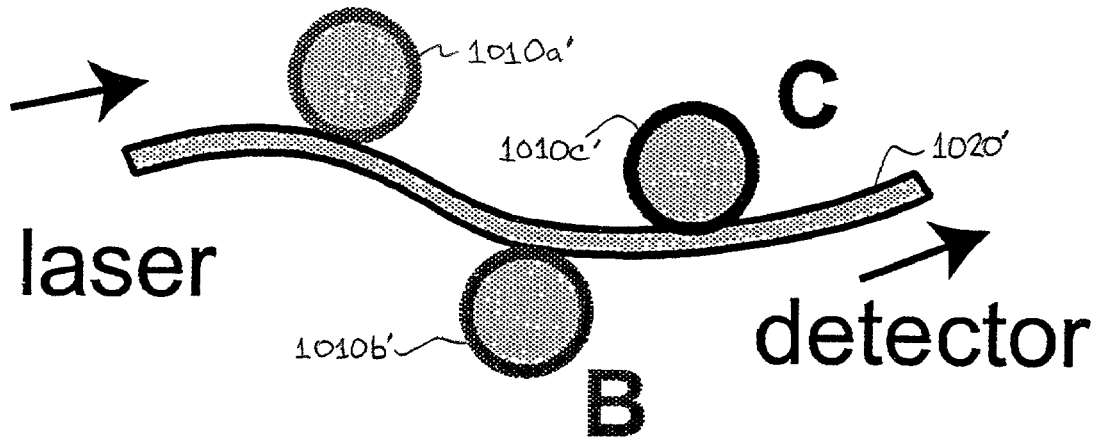
FIG. 11 illustrates a multiple-sphere sensor in which one of three receptors is modified with a receptor A to attract a ligand A'.
Figure 13:
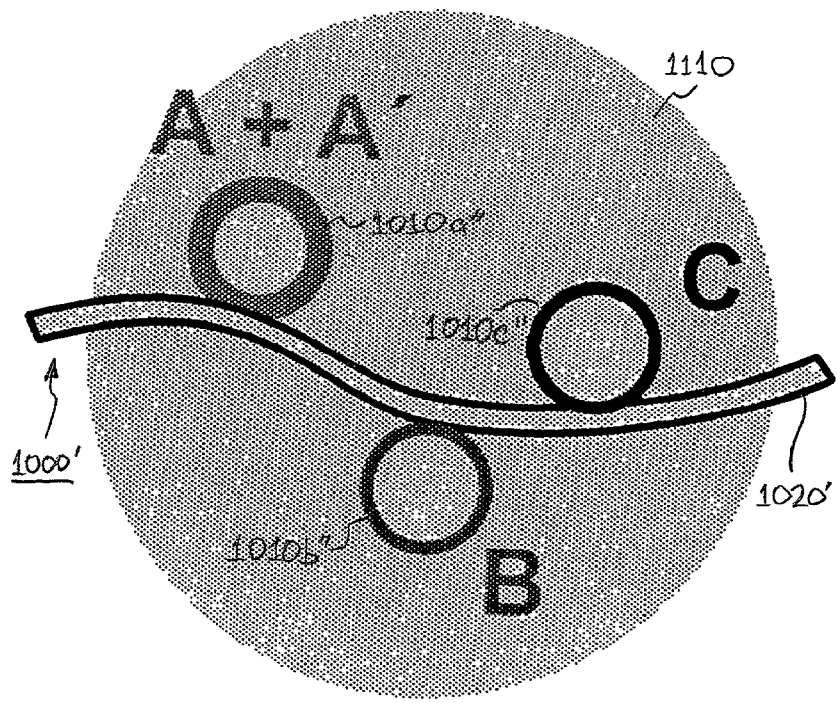
FIG. 13 illustrates the multiple-sphere sensor head of FIG. 11 placed into a solution including substance A'.
Figure 12A:
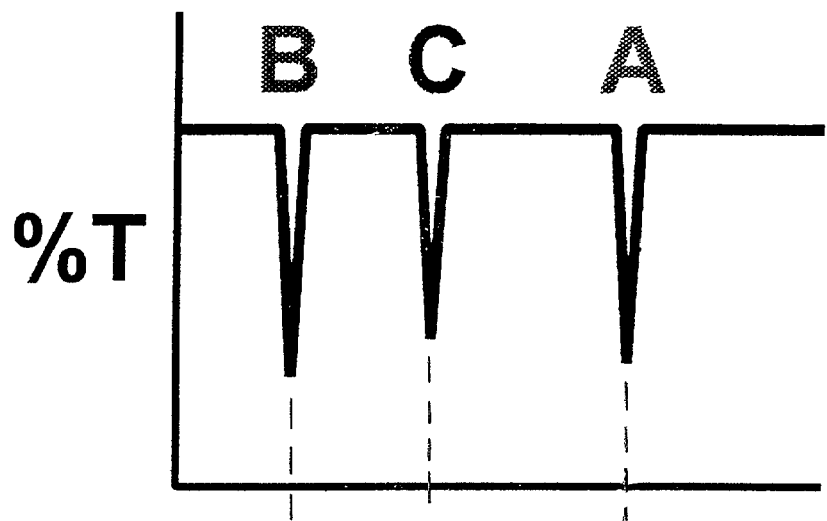
FIGS. 12A and 12B illustrate the frequency spectra of light detected through the sensors of FIGS. 11 and 13, respectively.
Figure 12B:
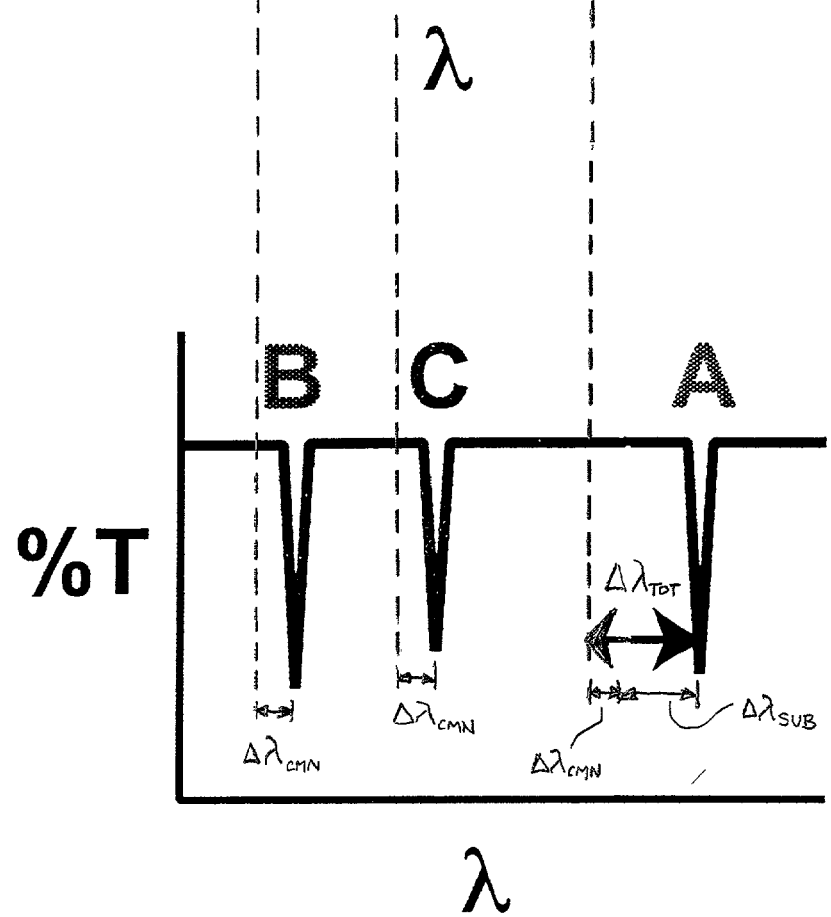

FIG. 11 illustrates a multiple-sphere sensing head 1000' including an optical fiber 1020' and three microspheres 1010a', 1010b' and 1010c'. The microsphere 1010a' is modified with a receptor for ligand A. FIG. 12A illustrates the dips in the frequency spectrum associated with a resonance frequency associated with each of the microspheres 1010a', 1010b' and 1010c'. Notice that the distinct dips can be used to distinguish the microspheres. FIG. 13 illustrates the multiple-sphere sensing head 1000' immersed in a solution 1100 containing substance A. Notice from FIG. 12B that all of the frequencies of all of the dips, associated with the resonant frequencies of the microspheres 1010a", 1010b' and 1010c' have all shifted to some extent due to common-mode noise, but the frequency of the dip associated with the resonant frequency of microsphere 1010a" will have also shifted (in the same or opposite direction as the shift due to the common-mode noise) due to the change in the size of microsphere 1010a" resulting from the adsorption of substance A. As can be seen in FIGS. 12A and 12B, the shift due to adsorption can be distinguished from that due to the noise.

§ 4.4.1.2 Exemplary Methods for Detecting and/or Measuring Substances

Exemplary methods for detecting and/or measuring substances using a single-sphere sensing head and a multiple-sphere sensing head, are described with reference to FIGS. 14 and 15, respectively.

Figure 1:
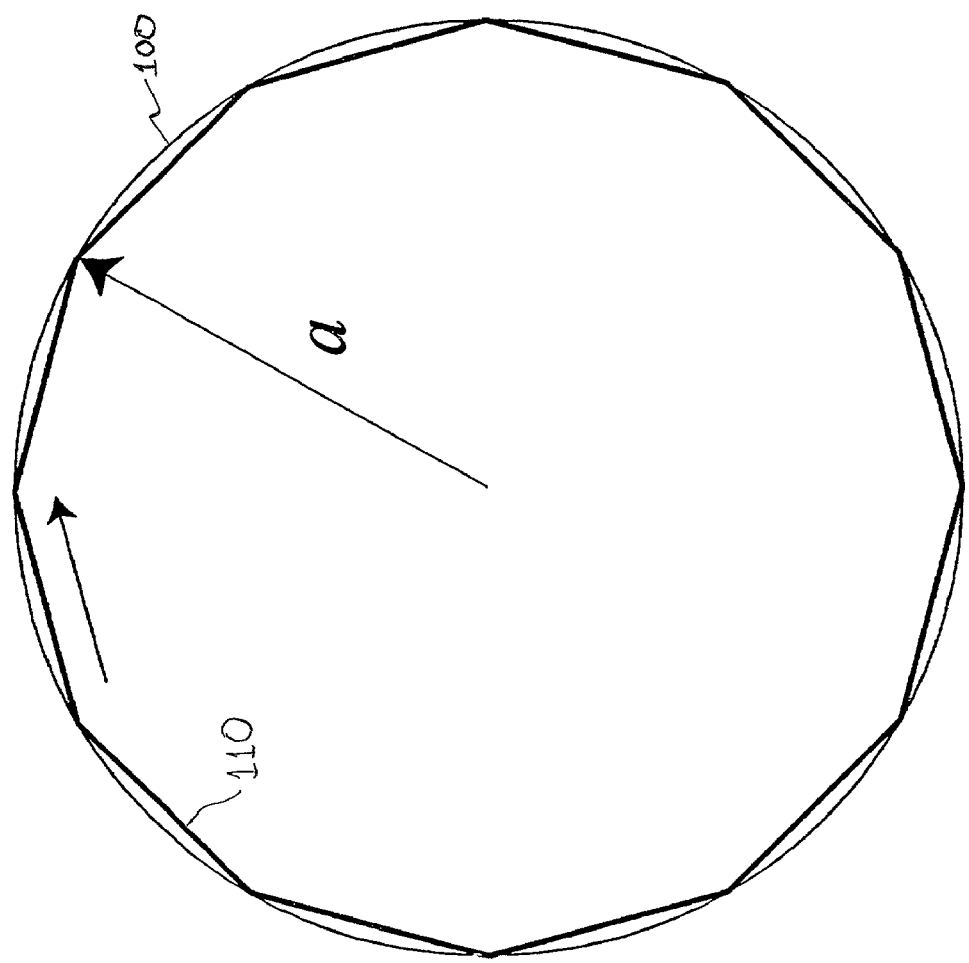
FIG. 1 is a cross sectional view of internal reflections in a microsphere.
Figure 2:
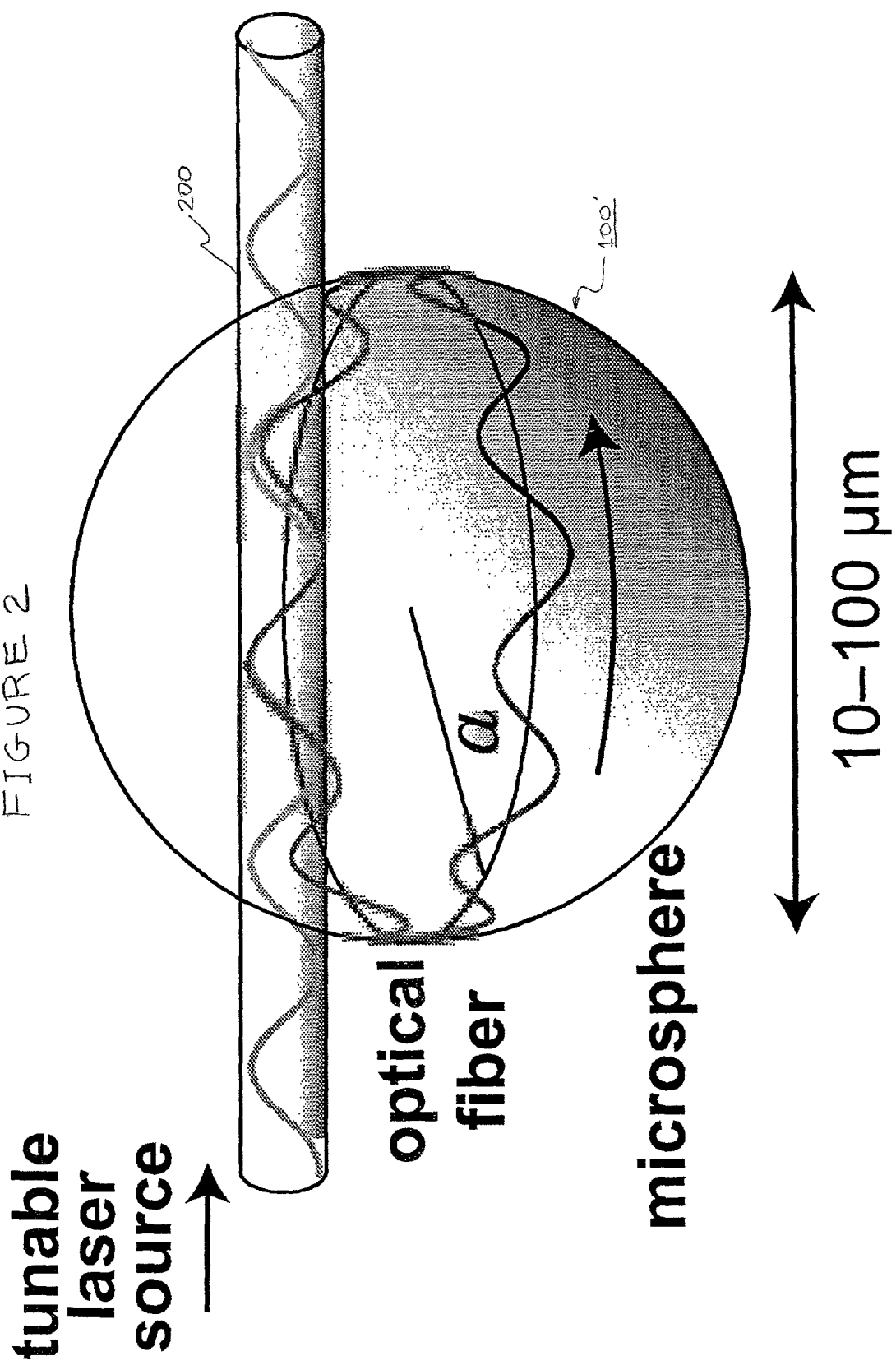
FIG. 2 illustrates the evanescent coupling of an optical fiber and a microsphere.
Figure 3:
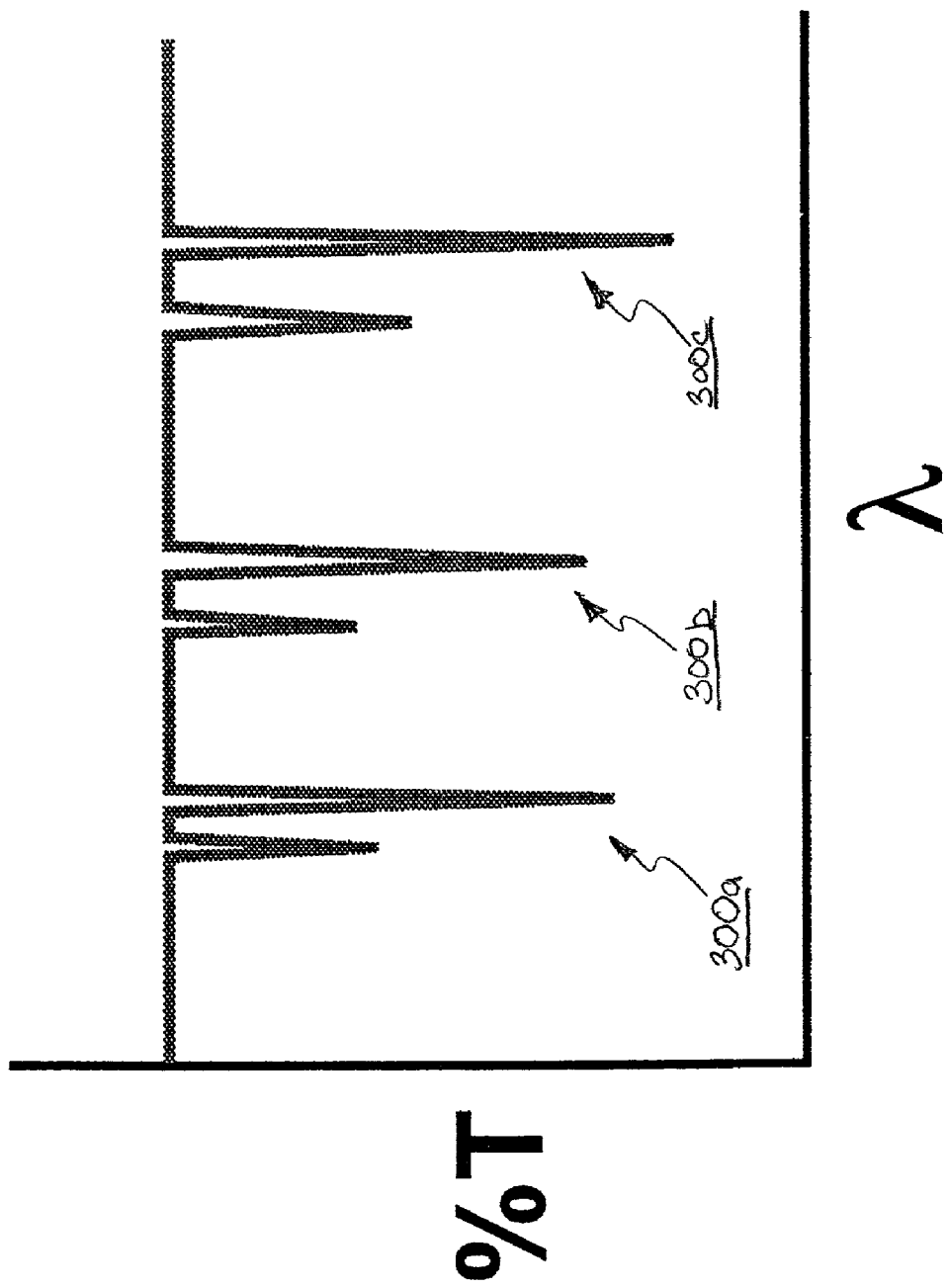
FIG. 3 illustrates transmission dips detected in light passing through an optical fiber evanescently coupled with a microsphere, such as that illustrated in FIG. 2.
Figure 14:
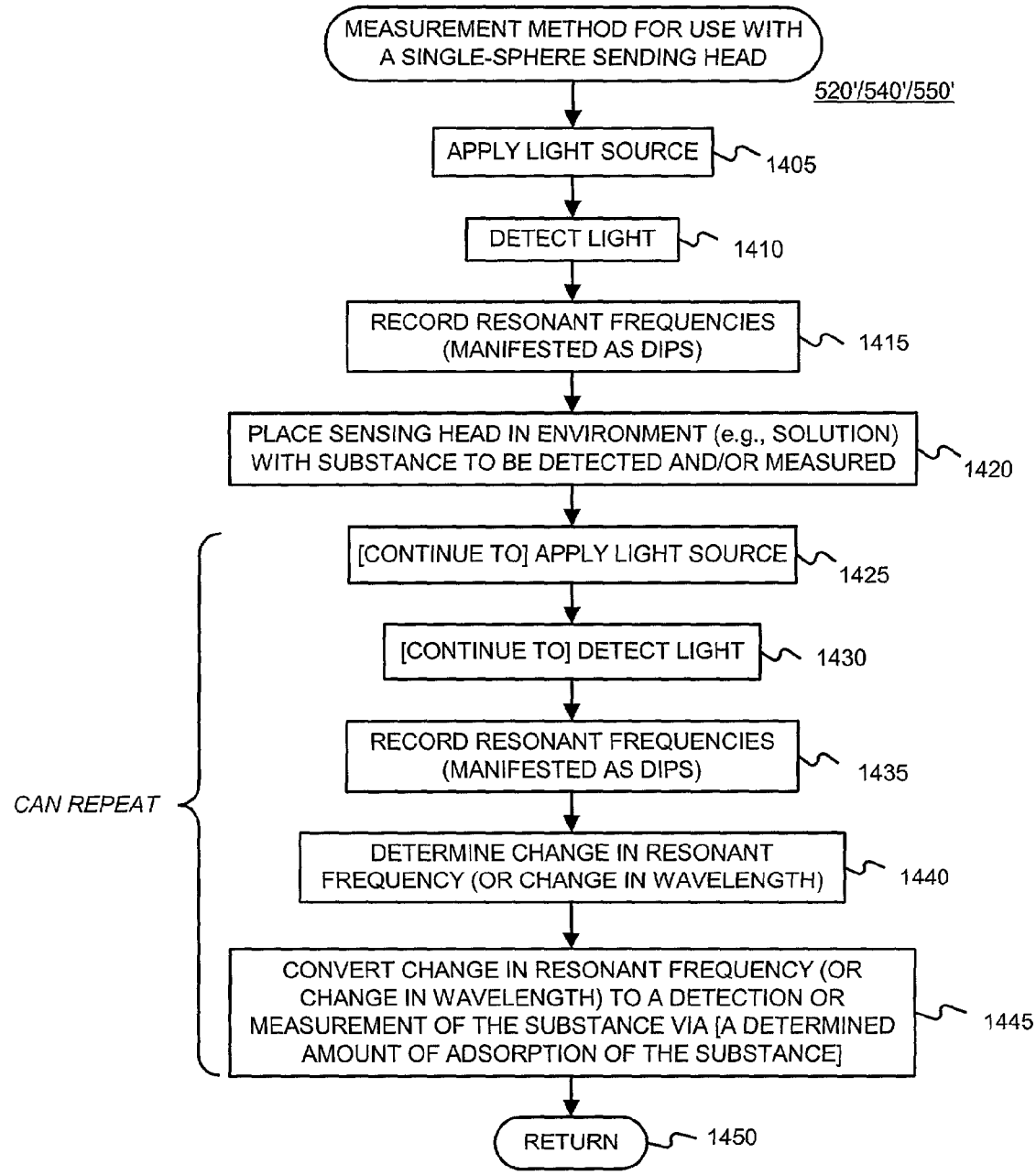
FIG. 14 is a flow diagram of an exemplary measurement method for use with a single-sphere sensing head.

FIG. 14 is a flow diagram of an exemplary method 520'/540'/550' that may be used to effect light sourcing operations 520, light detection operations 540, and substance detection and/or measurement operations 550 used with a single-sphere sensor head. The order in which the acts are performed is not intended to be limited by the order shown in FIG. 14. As shown in block 1405, a light source is applied. The light source may be a tunable laser, for example, and may be applied to a first fiber of single-sphere head sensor (Recall, e.g., 920 of FIG. 9.) or a first end of a fiber having an attached micro-sphere. As indicated by block 1410, light is detected. The light may be detected by a broadband, photodiode detector, for example, which may be coupled with a second fiber of a single-sphere head sensor (Recall, e.g., 930 of FIG. 9.), or with a second end of a fiber having an attached micro-sphere. The resonant frequencies, seen as dips (Recall, e.g., FIG. 3.), may be recorded, as indicated by block 1415. Then, as indicated by block 1420, the sensing head is placed in the environment (e.g., a solution) which may include the substance to be detected and/or measured. As was the case with blocks 1405 and 1410, a light source is (or continues to be) supplied and the resulting light is detected as indicated by acts 1425 and 1430, respectively. As was the case with block 1415, the resonant frequencies, seen as dips, may be recorded, as indicated by block 1435. The change in resonant frequency (or the change in the associated wavelength) is determined, as indicated in block 1440. This may simply be a matter of determining the differences between the dips before and after the sensing head is placed in the environment (e.g., solution) which may include the substance to be detected and/or measured. Finally, as indicated by block 1445, the determined change in resonant frequency (or determined change in the wavelength) are converted to a detection or measurement of the substance. As indicated by the bracket adjacent to blocks 1425 through 1445, these acts may be repeated to determine adsorption on other microspheres, for example, which may be converted to a concentration of another substance. The method may be left via RETURN node 1450.

Recall from § 4.4.1.1.3.2 above that by using a multiple-sphere sensing head, common-mode noise can be removed from the signal using wavelength screening and spectrum interpretation. That is, since the frequencies of all of the dips, associated with the resonant frequencies of the microspheres, all shift to some extent due to common-mode noise, but the frequency of the dip associated with the resonant frequency of a microsphere with receptors will also shift (in the same or opposite direction as the shift due to the common-mode noise) due to the change in the size of that microsphere resulting from the adsorption of a substance, the shift due to adsorption can be distinguished from that due to the noise.

Figure 15:
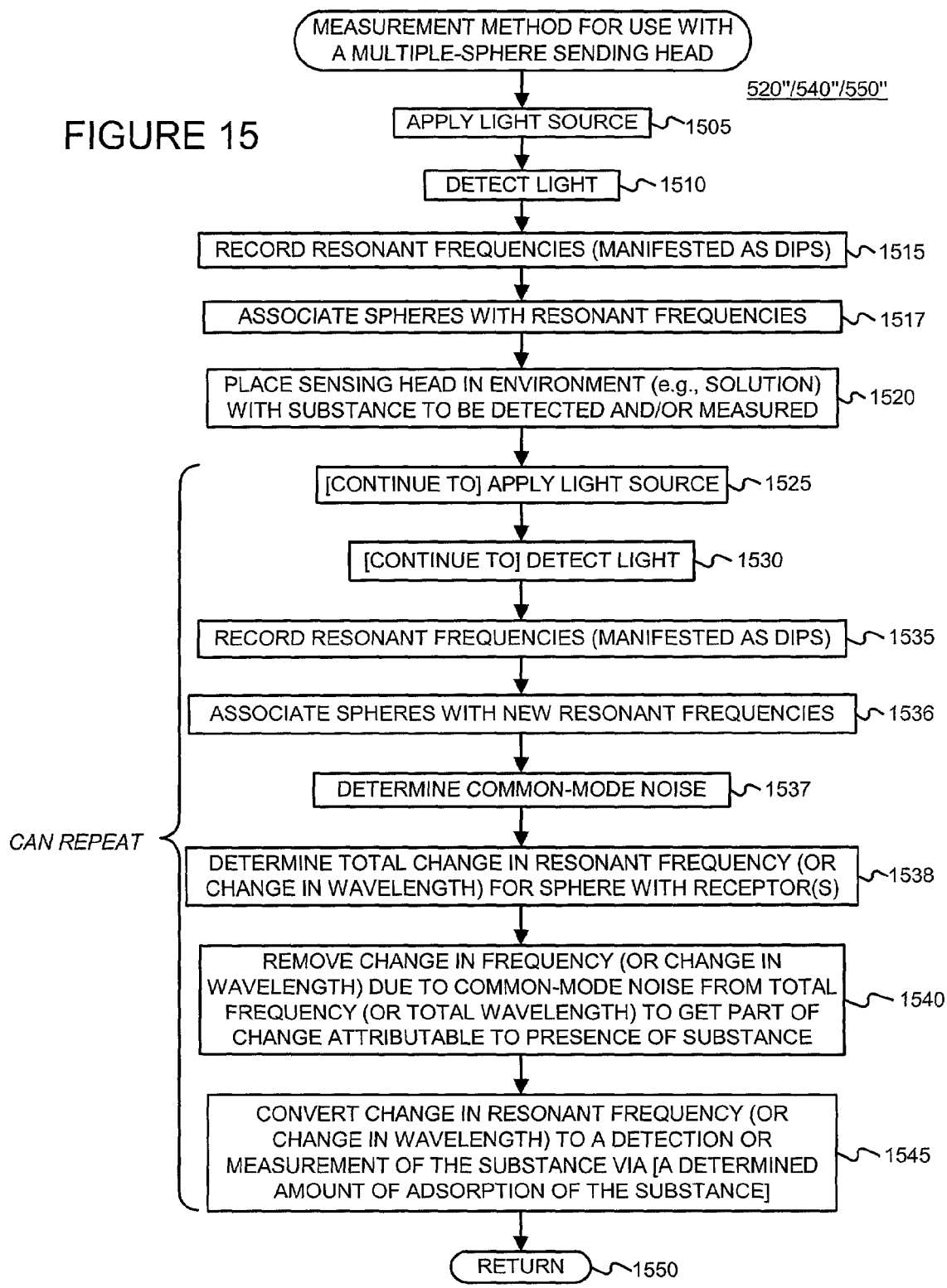
FIG. 15 is a flow diagram of an exemplary measurement method for use with a multiple-sphere sensing head.

FIG. 15 is a flow diagram of an exemplary method 520"/540"/550" that may be used to effect light sourcing operations 520, light detection operations 540, and substance detection and/or measurement operations 550 used with a multiple-sphere sensor head. The order in which the acts are performed is not intended to be limited by the order shown in FIG. 15. As shown in block 1505, a light source is applied. The light source may be a tunable laser, for example, and may be applied to a first end of a fiber having attached micro-spheres (Recall, e.g., FIG. 11.). As indicated by block 1510, light is detected. The light may be detected by a broadband photodiode detector, for example, which may be coupled with a second end of the fiber having the attached micro-spheres. The resonant frequencies, seen as dips (Recall, e.g., FIG. 12A.), may be recorded, as indicated by block 1515. These resonant frequencies are associated with the various microspheres as indicated by block 1517. This may be done by monitoring a transmission spectrum through the fiber. For example, recall from equation (1) that $\Delta\lambda$ is proportional to $\Delta a$. Resonance from two microspheres differing by $10^{-7}a$ should be easily distinguishable. Given that the standard deviation in "a" for emulsion polymerization of a polystyrene microsphere is $>10^{-2}a$, the resonance frequency of each microsphere, among ~1000 of microspheres, should be easily distinguished from those resonance frequencies of the other microspheres. Then, as indicated by block 1520, the sensing head is placed in the environment (e.g., a solution) which may include the substance to be detected and/or measured. As was the case with blocks 1505 and 1510, a light source is (or continues to be) supplied and the resulting light is detected as indicated by acts 1525 and 1530, respectively. As was the case with block 1515, the resonant frequencies, seen as dips, may be recorded, as indicated by block 1535. As was the case with block 1517, the resonant frequencies are associated with the microspheres, as indicated by block 1536.

Common-mode noise may then be determined, as indicated by block 1537. (Recall, e.g., FIGS. 12A and 12B.) The total change in resonant frequency (or the total change in wavelength) for the microsphere(s) provided with the receptor(s) is then determined as indicated by block 1538. Then, as indicated by block 1540, the amount of change in resonant frequency (or wavelength) due to common-mode noise is removed from the total change in resonant frequency (or wavelength) to obtain the part of the change attributable to the presence of the substance being detected and/or measured. Finally, as indicated by block 1545, the part of the determined change in resonant frequency (or determined change in the wavelength) attributable to the presence of the substance is converted to a detection or measurement of the substance. As indicated by the bracket adjacent to blocks 1525 through 1545, these acts may be repeated to determine a rate of adsorption, for example, which may be converted to a concentration of the substance. The method may be left via RETURN node 1550.

§ 4.4.2 Exemplary Methods, Apparatus and Compositions of Matter for Performing Operations Related to Fabricating Sensors Recall from FIG. 5 that the system 500 uses a sensor 530. Recall from FIGS. 9 and 11 that a sensor may be characterized as a single-sphere sensing head or a multiple-sphere sensing head. In each case, as summarized in FIG. 6, the fabrication of a sensor head involves two basic operations—and coupling the microsphere(s) and optical fiber(s), and attaching receptor(s) to a microsphere(s). Methods and apparatus that may be used to perform these operations, as well as the resulting sensors, are now described. Note that the methods, apparatus, and components used will often depend upon the ultimate application of the sensing head.

§ 4.4.2.1 Exemplary Materials for the Fiber and Microspheres

An inorganic glass, such as silica, or an amorphous polymer, such as poly(methyl methacrylate) ("PMMA"), are suitable materials for the optical fiber. Other known materials for optical fiber may be used.

The microsphere(s) can be any transparent material, such as silica, suffire, BK7, polystyrene, PMMA, polycarbonate, poly(ethylene terephthalate), etc. Spheres of different diameters are commercially available (such as from PolySciences, Inc., of Warrington, Pa.). For applications such as in vitro and in vivo measurement of chemicals in the blood vessel or body fluid, PMMA may be an appropriate material. Other polymers may also be suitable microsphere materials since they are inert in biological materials. Many polymers are also advantageously stable in acidic and basic environments. In such applications, the surface of the PMMA spheres may be modified to make them biocompatible and hypoallergenic. (See, e.g., Lasting Correction of Skin Defects and Wrinkles, http://www.canderm.com/artecoll/tech.html. With appropriate surface modifications, inorganic glasses may be also rendered biocompatible.

The microsphere(s) and the fiber may be made of the same material, though this is not necessary. However, it is preferable to keep the refractive indices of the microsphere(s) and fiber close to each other to promote phase matching.

§ 4.4.2.2 Exemplary Methods for Coupling the Fiber and Microsphere(s)

In the following, the term "connection" will be used to generally refer to all (e.g., mechanical, optical, electro-magnetic, etc.) interactions between a microsphere and a fiber. The term "coupling" will refer to the evanescent connection of a microsphere and a fiber, while the term "bridge" will refer, without loss of generality, to the mechanical connection of a microsphere and a fiber. Some theory related to desirable connection characteristics is first introduced in § 4.4.2.2.1. Then the affects of symmetry, distance, and mechanical bridging are described in §§ 4.4.2.2.2 through 4.4.2.2.4 below. Finally, some exemplary methods and compositions of matter for attaching the fiber and microsphere(s) are described in § 4.4.2.2.5.

§ 4.4.2.2.1 Optical Coupling Via Evanescent Field

Figure 16:
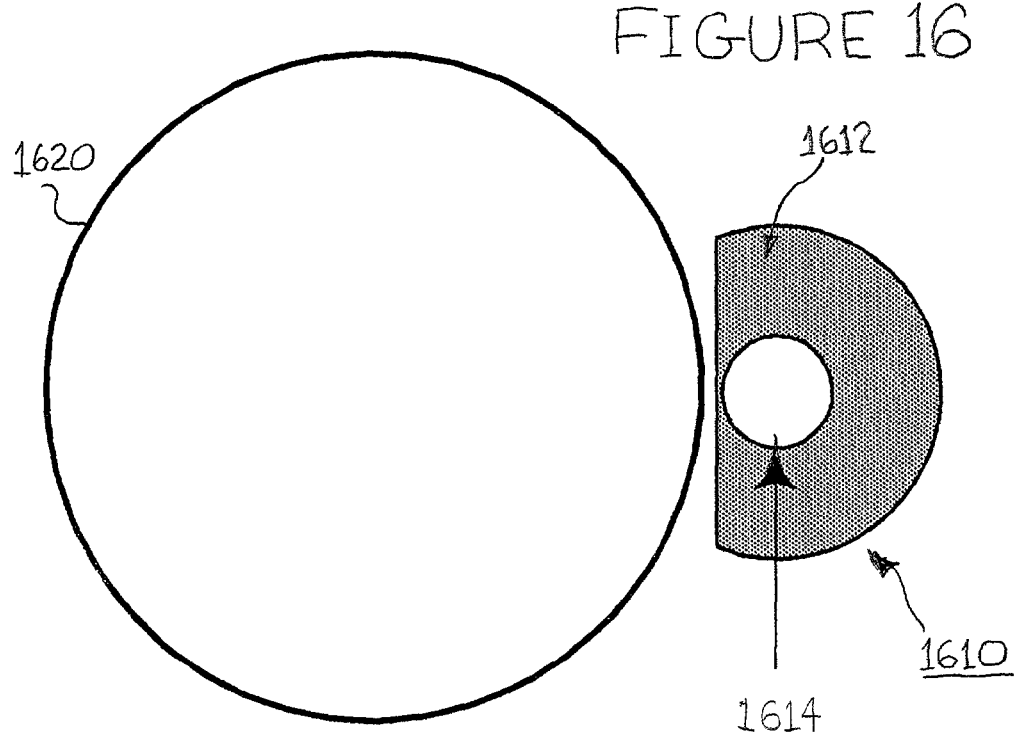
FIG. 16 is a cross-sectional end view of a microsphere coupled with an optical fiber.

By overlapping the evanescent field that surrounds a microsphere, and typically extends for a characteristic length of about 0.1 μm from the surface, with the evanescent field from the core of an optical fiber, (optical) coupling can be achieved. (See, e.g., the article A. Serpenguzel, S. Arnold, G. Griffel, J. A. Lock, Efficient Coupling of Guided Waves to Microsphere Resonances Using an Optical Fiber, J. Opt. Soc. B, 14, 790 (1997).) A cross-sectional end view of a basic half-coupler 1600 is illustrated in FIG. 16. In the half-coupler 1600, light is directed through the optical fiber 1610 (into the page). The fiber cladding 1612 is eroded to expose the evanescent field just outside the core 1614. The eroded fiber 1610 is pressed against the microsphere 1620.

§ 4.4.2.2.2 Effects of Symmetry of a Microsphere-to-Fiber Connection

Figures 17A, 17B:
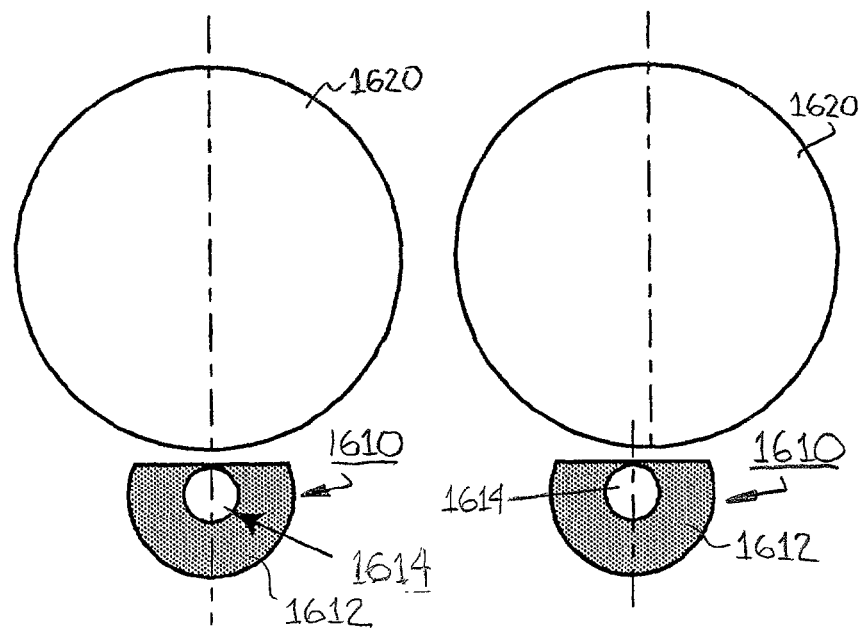
FIGS. 17A and 17B illustrate symmetric and asymmetric contact, respectively, between a microsphere and an optical fiber.
Figure 18:
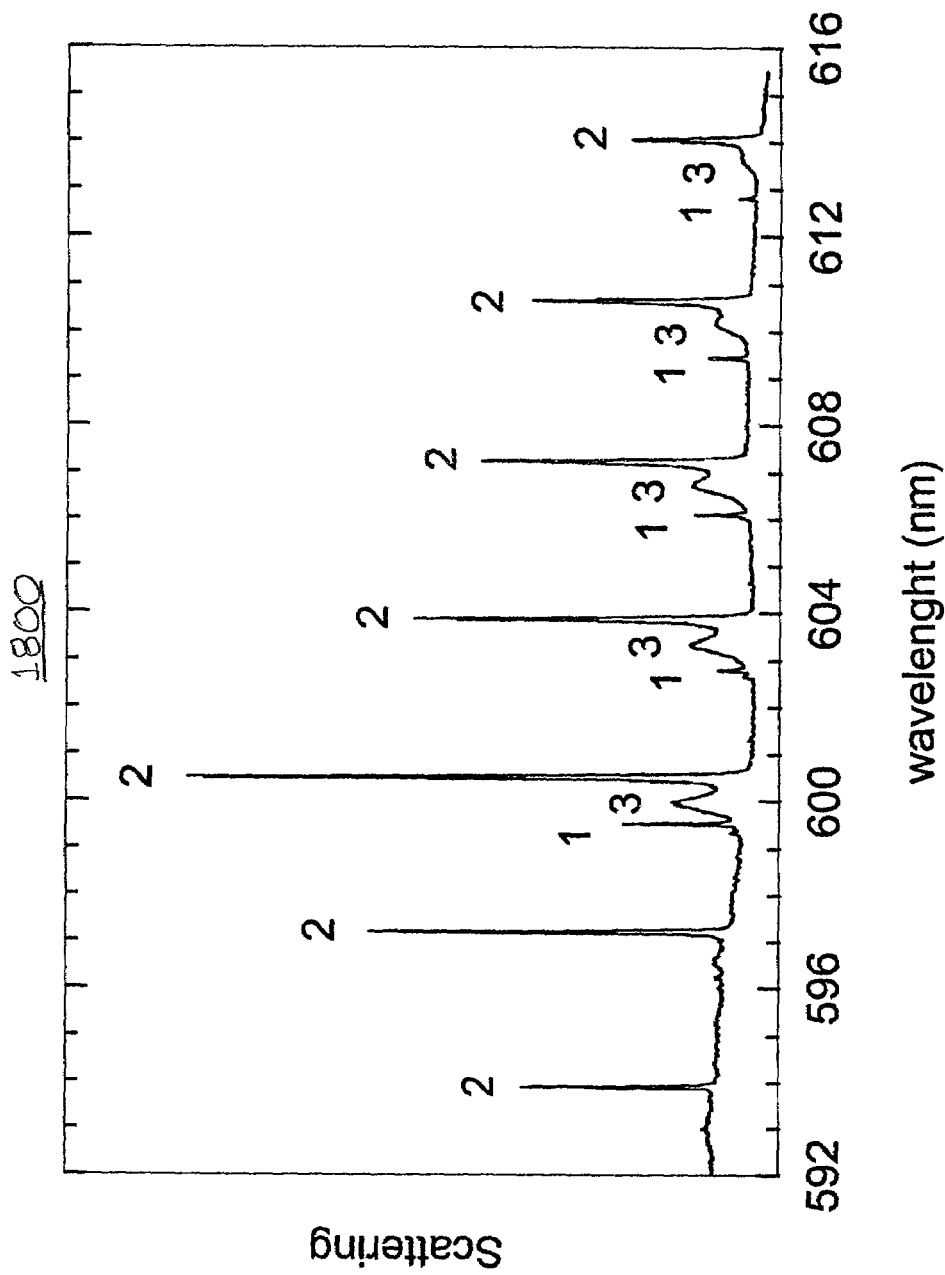
FIG. 18 is a resonance frequency spectrum of detected light that has passed through a sensing head.

It is desirable to provide a symmetric connection between the eroded fiber 1610 and the microsphere 1620, such as shown in FIG. 17A. If the center of the microsphere 1620 is not located above the center of the fiber core 1614, such as illustrated in FIG. 17B, coupling may be substantially attenuated. This was observed in the resonance spectrum, shown in FIG. 18, of an experimental system illustrated in FIG. 19.

Figure 19:
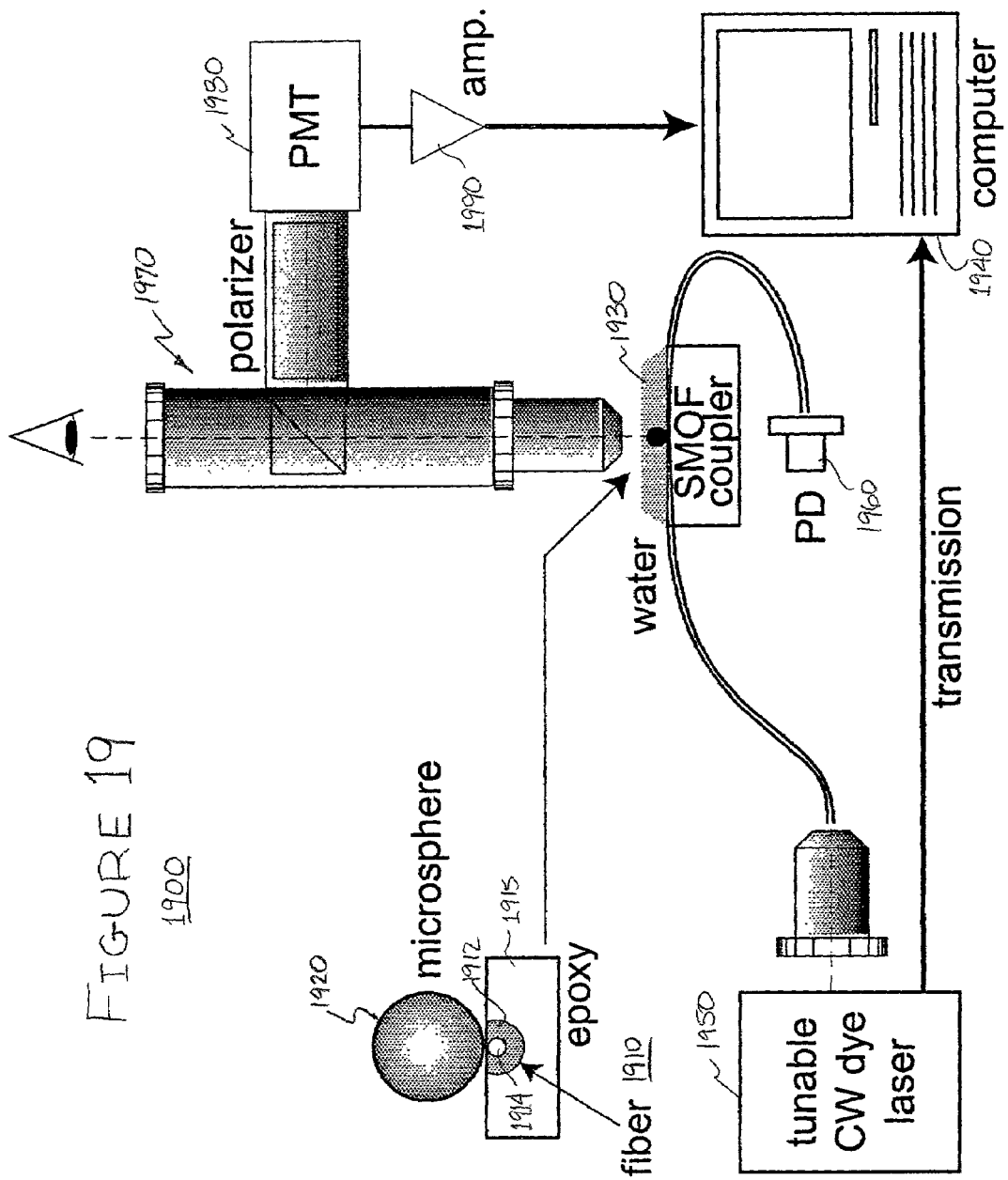
FIG. 19 illustrates an experimental system used to observe the resonance frequencies of a microsphere connected with an optical fiber.

More specifically, in the experimental system 1900 of FIG. 19, a fiber 1910 was epoxied to a Lucite block 1915. The combination was sanded and polished to eliminate most of the cladding 1912 from one side of the fiber 1910. Light from a tunable dye laser 1950 was coupled into the fiber with a polystyrene microsphere 1920 having a radius ≅15 μm. The microsphere 1920 was immersed in water. In one experiment, no scattering (i.e., radiation leakage) was observed from the microsphere 1920 until the wavelength was tuned to resonance, although scratches on the polished surface caused a small amount of background scattering. As indicated on the detected spectrum 1800 of FIG. 18, three orders of resonance occurred, the narrowest of which was essentially the same as that of the dye laser resolution (e.g., 0.025 nm). Note that the nearly periodic repeating resonance of a given order are associated with the mode number. Since the measured spectrum is a convolution of the intrinsic resonance line and the laser line, the actual resonance width is considerably narrower than measured. Wave theory can be used to predict the position of all of the resonance in the spectrum 1800 using just one adjustable parameter "a". Note, however, that near the beginning of the resonance spectrum 1800, the first-order modes are not present.

Such undesirable asymmetric contact may occur if the microsphere (a) is improperly positioned, and/or (b) moves (e.g., rolls) out of position. To secure the symmetric coupling between the evanescent fields of the microsphere and the fiber by ensuring symmetric contact such as that illustrated in FIG. 17A, a polymer microsphere may be attached, covalently, with the eroded fiber. Details of the covalent attachment are given in 4.4.2.2.5.

§ 4.4.2.2.3 Effects of Separation Distance of a Microsphere-to-Fiber Connection In addition to the desirability of symmetric coupling, the distance between the microsphere and fiber core will also affect performance. More specifically, if the microsphere and fiber core are too far apart, the coupling of their respective evanescent fields may be insufficient. If, on the other hand, the microsphere and fiber core are too close, the presences of the fiber's evanescent field may change the boundary condition of the microsphere, thereby undermining the inherently high quality factor (Q) of the resonance. However, the inventors have found that permitting the microsphere and fiber core to contact one another is acceptable in some applications.

§ 4.4.2.2.4 Effects of the Bridging of a Microsphere-to-Fiber Connection

Further, the bridge physically coupling the microsphere(s) and the fiber should be mechanically strong and durable. However, the coupling should minimize the perturbation to the resonating state of the photon(s) in the microsphere. Thus, for example, a bridge coupling each microsphere with the fiber should be small.

§ 4.4.2.2.5 Exemplary Methods and Compositions of Matter for Attaching the Fiber and Microsphere(s)

Figure 20:
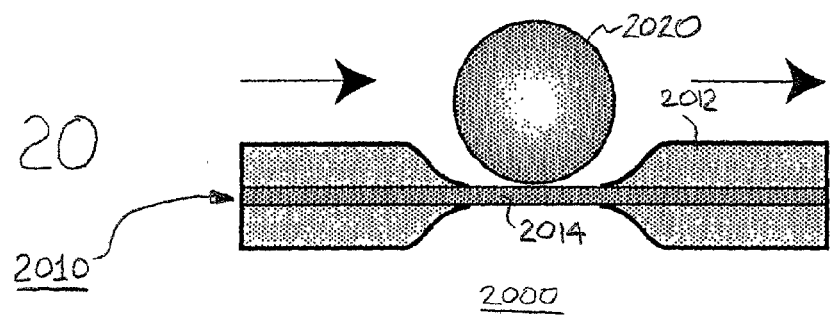
FIG. 20 is a cross-sectional end view of a microsphere coupled onto a cylindrically eroded fiber.
Figure 21A:
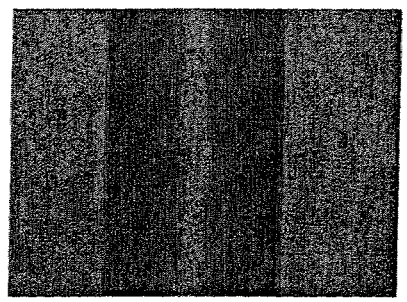
FIGS. 21A and 21B illustrate a silica fiber with cladding and cylindrically eroded cladding, respectively.
Figure 21B:

FIG. 20 is a cross-sectional side view of a sensing head (section) 2000 including an attached microsphere 2020 and fiber 2010. To locate the microsphere 2020 symmetrically, with respect to the fiber core 2014, the fiber 2010 was eroded on all sides (referred to as "cylindrical erosion"). Such cylindrical erosion of the cladding 2012 can be effected by etching the fiber 2010 at a desired region or regions with a hydrofluoric acid solution or a base solution, thereby exposing the evanescent field of the fiber core 2014. In one exemplary fabrication method, the etching was terminated when the amplitude of a laser transmitting through the fiber showed a hint of decrease. As illustrated in FIGS. 21A and 21B, a silica fiber with cladding had an initial total diameter of ~125 μm, before being eroded to a diameter of ~6 μm. The final diameter can be controlled by changing the concentration of the acid or the base and the etching time.

Plastic fiber may be eroded by immersing it into a solvent that dissolves the cladding. For example, a PMMA fiber with a fluoropolymer cladding (available from Mitsubishi Rayon and Toray) can be eroded in a solution of hexafluoroisopropanol.

Other methods for exposing evanescent field of the core of the optical fiber will be apparent to those skilled in the art. Now, exemplary methods and compositions of matter for attaching a microsphere to a fiber are described. Generally though, the microspheres may be connected to the eroded fiber with techniques used by biochemists for attaching microspheres to microscope slides (See, e.g., F. J. Steemers, J. A. Ferguson, D. R. Walt, Screening Unlabeled DNA targets with Randomly Ordered Fiber Optic Gene Arrays, Natur. Biotech. 18, 91 (2000).), or by other silanization methods (See, e.g., The Colloid Chemistry of Silica, H. E. Bergna, ed. Adv. Chem. Ser. 234, Amer. Chem. Soc. (1994); E. P. Plueddemann, Silane Coupling Agents Kluwer (1990).).

In a first example, a siloxane network may be used to bridge a silica fiber and a silica microsphere. More specifically, a tiny amount (e.g., ~Pico liter) of tetramethozysilane or dimethyldimethoxysilane may be applied (e.g., dropped) into a space between a microsphere and the fiber, followed by dehydration and baking in an oven. (See, e.g., E. P. Plueddemann, Silane Coupling Agents Kluwer (1990).) The resultant fiber-sphere pair is chemically identical to bare silica.

In a second example, amide and other bonds may be used to bridge a silica microsphere and a silica fiber. More specifically, surface silanols on the microsphere and fiber can be converted to primary amines. Consequently, the two amines will be bonded by acid anhydride or dialdehyde. Silica surface has a high density of reactive silanols (~0.05 Å$^{-2}$), or can at least be modified to have silanols at high density by washing in hydrochloric acid and rinsing followed by heating. Amino silanation will be accomplished by reacting silanols with amino silanation agencies such as aminopropyl trimethoxysilane. The silanation methods have been widely used to make glass fiber compatible to a plastic matrix to prepare fiber-reinforced plastic. (See, e.g., the article E. P. Plueddemann, Silane Coupling Agents Kluwer (1990).) Bridging two amines with acid anhydride such as succinic anhydride or dialdehyde such as glutaraldehyde is widely used in biochemistry. (See, e.g., the article J. McCafferty, H. R. Hoogenboom, D. J. Chiswell Ed., Antibody Engineering, IRL Press (1996).)

Instead of amine modification, the silica surface can be modified with carboxylic acid (by aminopropyl modification followed by reaction with succinic anhydride) and bridge two acids with carbodiimide.

The two foregoing methods form similar functional groups on both the fiber and microsphere. The inventors believe that one of these functional groups can be modified with amine and the other of these functional groups can be modified with carboxyl, so that the contact points can convert to amide bonds.

Amide bond formation is advantageous in that (i) the bonds are formed only where the sphere and fiber are in contact, and (ii) the resultant microsphere-fiber complex retains reactive surface moieties for further biochemical and biological functionalization.

In a third example, a plastic fiber is connected with a plastic microsphere. PMMA spheres having a carboxylated surface are commercially available, in various diameters, from PolySciences Inc. of Warrington, Pa. However, the PMMA core of optical fiber does not have a carboxylated surface (not functionalized). Carboxylic acid may be attached to the optical fiber core by coating the eroded fiber with a copolymer of methyl methacrylate and acrylic acid in solution, followed by annealing. Thereafter, bridging the two carboxylic groups can be done in the same manner as described above for bridging silica.

A tiny amount of silanization agent and a bridging agent may be provided (e.g., dropped), for example with a Pico liter jet (See, e.g., the article S. Arnold, L. M. Folan, A Fluorescence Spectrometer for a Single Electrodynamically Levitated Microparticle, Rev. Sci. Inst. 57, 2250 (1986).) onto the microsphere-fiber core contact.

Referring back to FIG. 9, a slightly spheroidal fused silica bead can be formed at the end of silica fibers by melting it with a microtorch. (See, e.g., the article V. B. Braginsky, M. L. Gorodetsky, V. S. Ilchenko, Quality-Factor and Nonlinear Properties of Optical Whispering-Galley Modes, Phys. Lett. A, 137, 393 (1989).) In one experiment, a quality factor (Q) of $3 \times 10^7$ was maintained for such a sensing head 900.

§ 4.4.2.3 Providing Receptor on Microsphere(s)

Recall that the surface of a microsphere used to detect a substance will be modified with a receptor to interact with that substance (a specific ligand). Naturally, the receptor used will depend upon the particular application for which the sensor head is to be used. Various exemplary microsphere-receptor combinations are described below.

In a first example, the microsphere is modified to adsorb a specific ligand. First, surface silanols are functionalized onto the microsphere. Then, a secondary modification is used to attach the biochemical substance complementary to the specific ligand to be detected. The coupling utilizes reactions between two amines, two acids, or amine and acid. Amino groups naturally present in proteins can be coupled directly to the surface carboxyl or with glutaraldehyde to the surface amine. Attaching glucose oxidase to the microsphere surface will allow the detection of glucose for instance.

In a second example, it is desired to detect RNA and single-stranded DNA fragments. In such an application, the microspheres may be provided with complementary oligonucleotides covalently bonded to their surface. Covalent bonding will be furnished by coupling nucleotides (with alkylamine extended on the 5' end) with the surface amine using glutaraldehyde. When used in a system such as that of FIG. 5, such microspheres would experience a shift in their optical resonance when hybridized with complementary strands. Adsorbates which are not complementary may be washed away. By preparing a plurality of microspheres with different oligonucleotide modifications and arranging them along an optical fiber to provide a multiple-sphere sensing head, it is possible to identify the base sequence in a given DNA sample. Such a sensing head could be calibrated by adding a known complementary oligonucleotide and observing the corresponding dip in the spectrum shifts. The bound oligonucleotides can then be removed, for instance, by subsequent heat denaturing. In this way, single-molecule detection, with or without fluorescence labeling, is possible.

In a third example, it is desired to detect the presence of an antigen such as carcinoembryonic (CEA) antigen and HSA (human serum albumin), etc. . In such an application, an antibody or antibodies such as anti-CEA and anti-HSA, etc. may be covalently attached to the surface of a microsphere. Conversely, presence of antibody may be detected by attaching its antigen molecules onto the surface.

In a fourth example, it is desired to detect the presence of a substrate and/or inhibitor. In such an application, the surface of a microsphere may be provided with an enzyme. For example, if glucose oxidase is immobilized onto the surface of a microsphere, such a sensing head could be used in a system, such as that illustrated in FIG. 5, for detecting the concentration of glucose. In another example, lipase immobilized onto the surface of a microsphere will be able to detect the presence of magnesium ion, an inhibitor of the enzyme.

§ 4.5 Conclusions

It is clear from the foregoing that the present invention provides a small, highly-sensitive with a high quality factor (Q), sensing head and system for detecting and/or measuring various substances, such as biochemical substances. The resolution and dynamic range of the resonance far exceeds those of existing detection schemes. Indeed, the high quality factor (Q) detection enables unprecedented opportunities for microscale sensing. Common-mode noise can be determined and removed by using a multiple-sphere sensing head. By modifying the surface of the microsphere with biological receptors, the sensing head will interact with specific biological ligands, allowing detection of the presence or the concentration of the ligands.

What is claimed is:

1. For use in a system including a light source, and a light detector, for determining the presence or concentration of a substance in a medium, a sensor comprising:
    a) at least one optical fiber;
    b) a plurality of microspheres, each of the plurality of microspheres being coupled with the optical fiber, and at least one of the microspheres having a surface including receptors for the substance,
        wherein, when light is applied to the optical fiber, a resonance within each of the microspheres is excited,
        wherein, if the substance adsorbs to the receptors on a surface of one of the microspheres, a shift in the resonance occurs,
        wherein a presence or concentration of the substance can be determined based on the shift in resonance,
        wherein a resonance frequency of each of the plurality of microspheres can be distinguished from resonance frequencies of the other of the plurality of microspheres, and
        wherein a quality factor of the resonance excited within at least one of the microspheres by the light applied to the optical fiber is at least $10^5$.

2. The sensor of claim 1 wherein the substance is one of RNA and single stranded DNA, and
    wherein the receptors are complementary oligonucleotides.

3. The sensor of claim 2 wherein the complementary oligonucleotides are covalently bonded to the surface of at least one of the plurality of microspheres.

4. The sensor of claim 1 wherein the substance is an antigen, and
    wherein the receptors are antibodies.

5. The sensor of claim 4 wherein the antibodies are covalently bonded to the surface of at least one of the plurality of microspheres.

6. The sensor of claim 1 wherein the substance is one of a substrate and an inhibitor, and
    wherein the receptors are enzymes.

7. The sensor of claim 1 wherein the substance is glucose, and
    wherein the receptors are glucose oxidase.

8. The sensor of claim 1 wherein the optical fiber is an inorganic glass.

9. The sensor of claim 8 wherein the optical fiber is silica.

10. The sensor of claim 1 wherein the optical fiber is an amorphous polymer.

11. The sensor of claim 10 wherein the optical fiber is polymethyl methacrylate.

12. The sensor of claim 1 wherein the optical fiber is silica,
    wherein at least one of the plurality of microspheres is silica; and
    wherein the at least one microsphere and optical fiber are bridged by a siloxane network.

13. The sensor of claim 1 wherein the optical fiber is silica,
wherein at least one of the plurality of microspheres is silica, and
wherein the at least one microsphere and optical fiber are bridged by amine and other bonds.

14. The sensor of claim 13 wherein the other bonds bridge the amines, and are selected from a group consisting of acid anhydride, succinic anhydride, dialdehyde, and glutaraldehyde.

15. The sensor of claim 1 wherein the optical fiber is polymethyl methacrylate,
wherein at least one of the plurality of microspheres is polymethyl methacrylate, and
wherein the at least one microsphere and optical fiber are bridged by a siloxane network.

16. The sensor of claim 1 wherein at least one of the plurality of microspheres has a radius on the order of 10 μm.

17. The sensor of claim 1 wherein at least one of the microspheres is coupled with the optical fiber in such a way that there is an evanescent connection of the at least microsphere and the optical fiber.

18. The sensor of claim 1 wherein at least one of the microspheres is coupled with the optical fiber in such a way that an evanescent field surrounding the at least one microsphere overlaps an evanescent field from a core of the optical fiber.

19. The sensor of claim 1 wherein at least one of the microspheres is coupled with the optical fiber in such a way that an evanescent field surrounding the at least one microsphere overlaps an evanescent field from a core of the optical fiber to provide a symmetric coupling between the evanescent fields.

20. The sensor of claim 1 wherein the resonance excited within the microsphere is a resonance of photons orbiting within the microsphere.

21. For use in a system including a light source, and a light detector, for determining the presence or concentration of a substance in a medium, a sensor comprising:
　a) an optical fiber;
　b) a microsphere
　　i) being coupled with the optical fiber,
　　ii) having a surface including receptors for the substance,
　wherein, when light is applied to the optical fiber, a resonance within the microsphere is excited,
　wherein, if the substance adsorbs to the receptors on the microsphere surface, a shift in the resonance occurs,
　wherein a presence or concentration of the substance can be determined based on the shift in resonance, and
　wherein a quality factor of the resonance excited within the microsphere by the light applied to the optical fiber is at least $10^5$.

22. The sensor of claim 21 wherein the substance is one of RNA and single stranded DNA, and
wherein the receptors are complementary oligonucleotides.

23. The sensor of claim 21 wherein the substance is an antigen, and
wherein the receptors are antibodies.

24. The sensor of claim 21 wherein the substance is one of a substrate and an inhibitor, and
wherein the receptors are enzymes.

25. The sensor of claim 21 wherein the substance is glucose, and
wherein the receptors are glucose oxidase.

26. The sensor of claim 21 wherein at least one of the microspheres is coupled with the optical fiber in such a way that an evanescent field surrounding the at least one microsphere overlaps an evanescent field from a core of the optical fiber to provide a symmetric coupling between the evanescent fields.

27. The sensor of claim 21 wherein the resonance excited within the microsphere is a resonance of photons orbiting within the microsphere.

28. For use in a system including a light source, and a light detector, for determining the presence or concentration of a substance in a medium, a sensor comprising:
　a) at least one optical fiber;
　b) at least one microsphere, the at least one microsphere
　　i) being coupled with the optical fiber,
　　ii) having a surface including receptors for the substance,
　wherein, when light is applied to the optical fiber, a resonance within the microsphere is excited,
　wherein, if the substance adsorbs to the receptors on the microsphere surface, a shift in the resonance occurs,
　wherein a presence or concentration of the substance can be determined based on the shift in resonance, and
　wherein the at least one microsphere is coupled with the optical fiber at a beveled surface of the optical fiber such that light directed through the optical fiber towards the at least one microsphere reaches the optical fiber at an angle greater than a critical angle, wherein the critical angle is the arcsine of the refractive index of the microsphere divided by the refractive index of the optical fiber.

* * * * *